US009152854B2

(12) United States Patent
Lee

(10) Patent No.: US 9,152,854 B2
(45) Date of Patent: Oct. 6, 2015

(54) IMAGE PROCESSING APPARATUS AND METHOD

(71) Applicant: SAMSUNG MEDISON CO., LTD., Gangwon-Do (KR)

(72) Inventor: Kwang-Hee Lee, Gangwon-Do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 75 days.

(21) Appl. No.: 13/760,847

(22) Filed: Feb. 6, 2013

(65) Prior Publication Data

US 2013/0202175 A1 Aug. 8, 2013

(30) Foreign Application Priority Data

Feb. 6, 2012 (KR) .......... 10-2012-0011793
Dec. 7, 2012 (KR) .......... 10-2012-0142309

(51) Int. Cl.
*G06K 9/00* (2006.01)
*A61B 8/08* (2006.01)
*G06T 7/60* (2006.01)
*G06K 9/36* (2006.01)

(52) U.S. Cl.
CPC .......... *G06K 9/00362* (2013.01); *A61B 8/0875* (2013.01); *A61B 8/5223* (2013.01); *G06T 7/602* (2013.01); *G06T 2207/10136* (2013.01); *G06T 2207/30008* (2013.01)

(58) Field of Classification Search
CPC ... G06T 7/0012; G06T 7/0042; G06T 7/0081; G06T 7/0083; G06T 2207/10081; G06T 2207/10088; G06T 2207/10132; G06T 2207/20148; G06T 2207/3008; G06T 2207/30044; G06K 9/36; G06K 9/46; A61B 6/505; A61B 8/0875

USPC ......... 382/128, 131, 132, 171, 173, 190, 203, 382/259

See application file for complete search history.

(56) References Cited

U.S. PATENT DOCUMENTS 5,602,935 A * 2/1997 Yoshida et al. ............... 382/132
6,249,692 B1 * 6/2001 Cowin .......................... 600/407
7,399,278 B1   7/2008 Ross (Continued)

FOREIGN PATENT DOCUMENTS

EP      2 194 505 A1    6/2010
EP      2194505 A1 *   6/2010
WO    2008/072157 A2    6/2008

OTHER PUBLICATIONS

Kim, et al. "A New Measurement Method of Femoral Anteversion Based on 3D Modeling." IEEE/EMBS 19th Conference. (1997): 418-421. Print.*
Extended European Search Report issued in European Patent Application No. EP 13153870.4 dated May 16, 2013.
European Office Action issued in European Application No. 13 153 870.4 dated Mar. 5, 2014.

(Continued)

*Primary Examiner* — Michael A Newman
(74) *Attorney, Agent, or Firm* — McDermott Will & Emery LLP

(57) ABSTRACT

An image processing apparatus and method. The image processing apparatus includes: a data acquisition device for acquiring image data of a subject including a target bone; and a data processor for acquiring binary image data by performing thresholding based on the image data, segmenting the binary image data into a plurality of segments by labeling, determining one of the plurality of segments as a target image based on image characteristics of the target bone, and measuring a length of the target bone based on the target image.

20 Claims, 8 Drawing Sheets

(56) References Cited

U.S. PATENT DOCUMENTS

| | | |
|---|---|---|
| 7,780,600 B2 | 8/2010 | Krantz et al. |
| 2006/0165268 A1* | 7/2006 | Kaus et al. .................... 382/128 |
| 2007/0047794 A1* | 3/2007 | Lang et al. .................... 382/132 |
| 2007/0081705 A1* | 4/2007 | Carneiro et al. .............. 382/128 |
| 2008/0188748 A1 | 8/2008 | Sonek et al. |
| 2009/0122060 A1* | 5/2009 | Porat et al. .................... 345/424 |
| 2010/0322495 A1* | 12/2010 | Collet-Billon et al. ........ 382/131 |
| 2011/0060247 A1* | 3/2011 | Payne et al. ................... 600/587 |
| 2011/0125016 A1* | 5/2011 | Lazebnik et al. .............. 600/443 |
| 2011/0196236 A1* | 8/2011 | Swamy et al. ................. 600/443 |
| 2011/0224546 A1* | 9/2011 | Lee et al. ...................... 600/443 |
| 2011/0304332 A1* | 12/2011 | Mahfouz ....................... 324/309 |
| 2011/0305379 A1* | 12/2011 | Mahfouz ....................... 382/131 |
| 2013/0272594 A1* | 10/2013 | Zelzer et al. .................. 382/131 |

OTHER PUBLICATIONS

D. Salpou et al., "Fetal age assessment based on 2nd trimester ultrasound in Africa and the effect of ethinicity," BMC Pregnancy and Childbirth, Biomed Central Ltd., vol. 8, No. 1, Oct. 30, 2008, pp. 1-11.

Office Action issued in European Application No. 13 153 870.4 dated Aug. 19, 2014.

J.G. Thomas et al. "Automatic Segmentation of Ultrasound Images Using Morphological Operators" IEEE Transactions On Medical Imaging, vol. 10, No. 2, Jun. 1991, p. 180-186.

Korean Office Action issued in Korean Application No. 10-2012-0142309 dated Apr. 20, 2015, with English translation.

Korean Office Action issued in Korean Application No. 10-2012-0142309 dated Feb. 25, 2015, with English translation.

* cited by examiner

IMAGE PROCESSING APPARATUS AND METHOD

CROSS-REFERENCE TO RELATED PATENT APPLICATION

This application claims the benefit of Korean Patent Application No. 10-2012-0011793, filed on Feb. 6, 2012 and Korean Patent Application No. 10-2012-0142309, filed on Dec. 7, 2012, in the Korean Intellectual Property Office, the disclosures of which are incorporated herein in their entirety by reference.

BACKGROUND OF THE INVENTION

1. Field of the Invention

The present invention relates to an image processing apparatus and method.

2. Description of the Related Art

An image processing apparatus may be used for a medical imaging device, such as an ultrasound imaging device, a computed tomography (CT) device, and a magnetic resonance imaging (MRI) device. For example, an image processing apparatus may be included in the medical imaging device.

An image processing apparatus may be used for fetal biometric measurements. The fetal biometric measurements may be performed to estimate fetal gestational age, evaluate fetal size, and monitor fetal growth. An example of fetal biometric measuring is measuring a length of a target bone, such as a thighbone. The measured length of the target bone is an essential element to predict fetal abnormalities.

Thus, an image processing apparatus for efficiently measuring a length of a target bone and an operating method thereof are required.

SUMMARY OF THE INVENTION

The present invention provides an image processing apparatus for efficiently measuring a length of a target bone and an operating method thereof.

According to an aspect of the present invention, there is provided an image processing apparatus including: a data acquisition device for acquiring image data of a subject including a target bone; and a data processor for acquiring binary image data by performing thresholding based on the image data, segmenting the binary image data into a plurality of segments by labeling, determining one of the plurality of segments as a target image based on image characteristics of the target bone, and measuring a length of the target bone based on the target image.

The image data may be volume data, and the data processor may analyze shapes of the plurality of segments, acquire one or more remaining segments from the plurality of segments based on the analyzed shapes, and determine one of the one or more remaining segments as the target image based on luminance values.

The data processor may acquire a magnitude of a first principle component, a magnitude of a second principle component, and a magnitude of a third principle component for each of the plurality of segments by performing principle component analysis (PCA) for each of the plurality of segments to analyze the shapes of the plurality of segments and may acquire the one or more remaining segments based on the magnitudes of the first to third principle components.

The data processor may obtain a tube-score defined based on the magnitudes of the first to third principle components for each of the plurality of segments and determine segments of which the tube-score is greater than a critical value from among the plurality of segments as the one or more remaining segments.

The tube-score may be defined by $$T_S = 1 - \frac{\lambda_2 - \lambda_3}{\lambda_1^2},$$

where $\lambda_1$ denotes the magnitude of the first principle component, $\lambda_2$ denotes the magnitude of the second principle component, and $\lambda_3$ denotes the magnitude of the third principle component.

The data processor may determine a segment o a luminance value is the greatest from among the one or more remaining segments as the target image.

The segment determined as the target image may be a segment of which a sum of luminance values of points belonging thereto is the greatest.

The data processor may determine a longitudinal section of the target image and measure the length of the target bone based on the longitudinal section.

The data processor may acquire a mean point corresponding to a mean coordinate of points belonging to the target image, acquire both end points farthest from each other on a vertical section of the volume data, which passes through the mean point, from among the points belonging to the target image, set spheres of which the centers are the both end points, acquire a first point and a second point corresponding to mean coordinates of points belonging to the spheres and the target image for the spheres, acquire a point of which a distance from the first point is equal to a distance from the second point from among the points belonging to the target image, set a sphere of which the center is the point, acquire a third point corresponding to mean coordinates of points belonging to the sphere and the target image, and determine a section passing through the first, second, and third points as the longitudinal section of the target image.

The data processor may measure the length of the target bone based on a distance between the first and second points.

The data processor may acquire an adaptive threshold value based on a mean and a standard deviation of luminance values based on the image data and acquire the binary image data by performing the thresholding based on the adaptive threshold value.

The data processor may perform top-hat transformation and contrast enhancement based on the image data before performing the thresholding.

The data processor may perform denoising on the image data before performing the top-hat transformation.

The image data may be two-dimensional image data, and the data processor may determine a segment of which a luminance value is the greatest from among the plurality of segments as the target image. The segment determined as the target image may be a segment of which a sum of luminance values of points belonging thereto is the greatest.

The data processor may detect both end points in a long axis of the target image and measure the length of the target bone based on a distance between the both end points.

According to another aspect of the present invention, there is provided an image processing method including: acquiring image data of a subject including a target bone; acquiring binary image data by performing thresholding based on the image data; segmenting the binary image data into a plurality of segments by labeling; determining one of the plurality of segments as a target image based on image characteristics of the target bone; and measuring a length of the target bone based on the target image.

According to another aspect of the present invention, there is provided a non-transitory computer-readable storage medium having stored therein program instructions, which when executed by a computer, perform the image processing method.

DETAILED DESCRIPTION OF THE INVENTION

Reference will now be made in detail to embodiments, examples of which are illustrated in the accompanying drawings.

Figure 1:
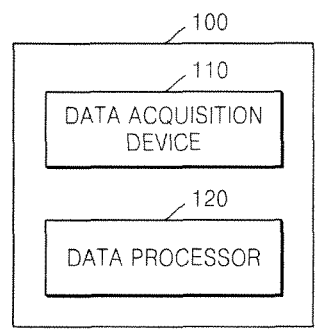
FIG. 1 is a block diagram of an image processing apparatus according to an embodiment of the present invention.

FIG. 1 is a block diagram of an image processing apparatus 100 according to an embodiment of the present invention.

Referring to FIG. 1, the image processing apparatus 100 includes a data acquisition device 110 and a data processor 120.

The image processing apparatus 100 may be used for a medical imaging device, such as an ultrasound imaging device, a computed tomography (CT) device, and a magnetic resonance imaging (MRI) device. For example, the image processing apparatus 100 may be included in the medical imaging device.

The data acquisition device 110 may acquire image data of a subject. The subject may be an animal body including a human body or a portion of an animal body. In addition, the subject includes a target bone, which has a long and thin tube shape. For example, the subject may be a pregnant woman, and the target bone may be a long bone, such as a fetal thighbone. The image data may be two-dimensional image data for imaging a cross-section of the subject or volume data for three-dimensionally imaging a three-dimensional space in the subject.

The two-dimensional image data may be a plurality of pixel values, and the volume data may be a plurality of voxel values. Each of the plurality of pixel values may be a luminance value of a corresponding pixel, and each of the plurality of voxel values may be a luminance value of a corresponding voxel. Hereinafter, for convenience of description, a point is used as the term indicating a pixel or a voxel.

The data acquisition device 110 may acquire image data by scanning the subject using an ultrasound signal or the like but is not limited thereto. As another example, the data acquisition device 110 may receive scan information obtained by scanning the subject from a scan device outside the image processing apparatus 100 and acquire image data based on the scan information. As another example, the data acquisition device 110 may receive image data from an external device. However, the data acquisition device 110 is not limited thereto and may acquire image data using various other methods.

The data processor 120 may measure a length of the target bone by processing the image data. The data processor 120 may acquire binary image data by performing thresholding based on the image data, segment the binary image data into a plurality of segments by labeling, determine one of the plurality of segments as a target image based on image characteristics of the target bone, and measure the length of the target bone based on the target image.

First, a method of processing image data in the data processor 120 when the image data is two-dimensional image data will now be described.

Figure 2:
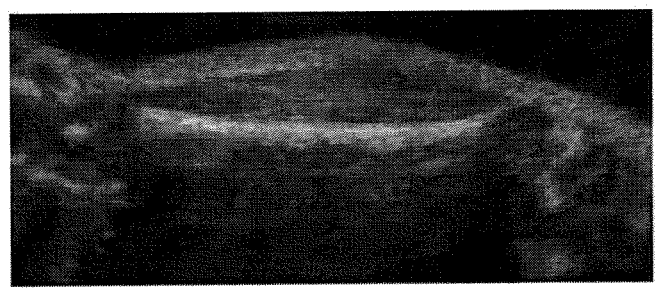
FIG. 2 illustrates a two-dimensional image generated using two-dimensional image data.

FIG. 2 illustrates a two-dimensional image generated using two-dimensional image data. The two-dimensional image of FIG. 2 is a B-mode ultrasound image.

Referring to FIG. 2, the two-dimensional image includes a target image that is an image of a target bone. However, a boundary of the target image in the two-dimensional image is not clear due to noise, an image of other tissue around the target bone, and so forth.

Thus, the data processor 120 may process the two-dimensional image as described below before performing thresholding.

The data processor 120 may acquire a pre-processed image by pre-processing the two-dimensional image. For example, the pre-processing may be performed by performing denoising based on a total variation (TV) algorithm.

Figure 3:
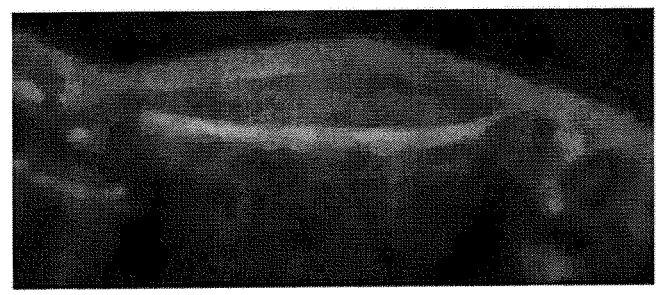
FIG. 3 illustrates an image pre-processed by performing denoising.

FIG. 3 illustrates an image pre-processed by performing denoising. Referring to FIG. 3, it may be seen that by performing the denoising, noise is removed, and an edge is maintained.

The denoising based on the TV algorithm is only illustrative, and the data processor 120 may remove noise from the two-dimensional image and enhance image quality by using various pre-processing methods. However, the data processor 120 may omit the pre-processing process.

The target image that is an image of the target bone has a thin and long shape, and a luminance value of the target image is greater than luminance values of other regions. Thus, to extract a bright region having a thin and long shape from the pre-processed image, the data processor 120 may perform top-hat transformation on the pre-processed image. If the pre-processing process is omitted, the data processor 120 may perform the top-hat transformation on a binary image.

The top-hat transformation h may be represented by Equation 1 below.

$$h = f - (f \circ b) \qquad (1)$$

In Equation 1, f denotes an input image, i.e., a pre-processed image, b denotes a structuring element, and $\circ$ denotes an opening operation.

Figure 4:
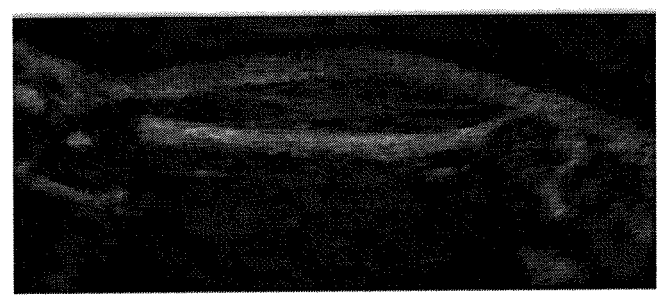
FIG. 4 illustrates a top-hat transformed image.

FIG. 4 illustrates a top-hat transformed image.

After the top-hat transformation, to more clearly distinguish the target image from the other regions by more clearly defining the edge of the target image, contrast enhancement may be performed on the top-hat transformed image.

For example, an image CEh(p) (where p denotes a point) obtained by applying the contrast enhancement to a top-hat transformed image of 256 gray levels may be acquired by Equation 2 below.

$$CEh(p) = \left(\frac{h(p) - \min}{\max - \min}\right) \times 255 \qquad (2)$$

In Equation 2, h(p) denotes a luminance value of a point p in a top-hat transformed image, and max and min denote a maximum luminance value and a minimum luminance value in the top-hat transformed image, respectively. In this case, since min is 0 or is approximate to 0, an appropriately small value, such as min=20, may be assigned to min.

Figure 5:
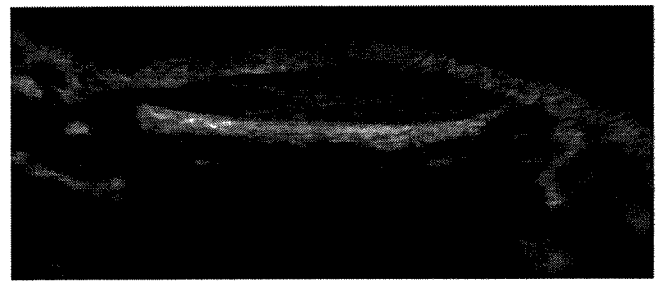
FIG. 5 illustrates a contrast-enhanced image.

FIG. 5 illustrates a contrast-enhanced image.

As such, the data processor 120 may perform the denoising, the top-hat transformation, the contrast enhancement, and so forth on the two-dimensional image.

Next, the data processor 120 may acquire a binary image g(p) to which an adaptive threshold is applied from the contrast-enhanced image CEh(p).

For example, the binary image g(p) may be acquired from the contrast-enhanced image CEh(p) by using Equation 3 below.

$$g(p) = \begin{cases} 1, & CEh(p) > T \\ 0, & CEh(p) \leq T \end{cases} \qquad (3)$$

In Equation 3, T denotes an adaptive threshold. That is, the binary image g(p) may be an image in which points whose luminance values in the contrast-enhanced image CEh(p) are greater than the adaptive threshold T are displayed white while the other points are displayed black.

The adaptive threshold T may be acquired based on a mean and a standard deviation of luminance values in the contrast-enhanced image CEh(p). For example, the adaptive threshold T may be acquired by Equation 4 below.

$$T = m + a \cdot s \qquad (4)$$

In Equation 4, m denotes a mean of luminance values in a contrast-enhanced image, s denotes a standard deviation of the luminance values, and a denotes a weight.

Figure 6:
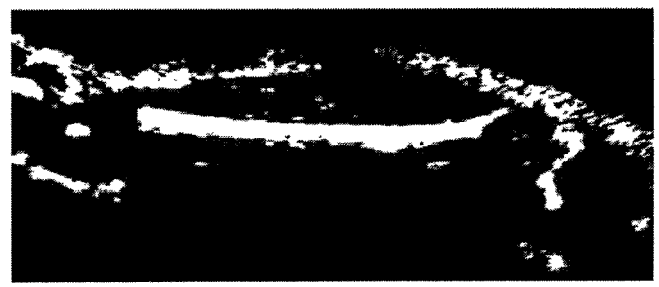
FIG. 6 illustrates a binary image.

FIG. 6 illustrates a binary image.

Referring to FIG. 6, although the binary image includes the target image, the binary image may include an image of other tissue having another shape.

Thus, the data processor 120 may process the binary image as described below to extract the target image.

The data processor 120 may segment binary image data into a plurality of segments by labeling. Each of the plurality of segments is a region including points whose luminance values are 1. The plurality of segments are candidates of the target image.

Figure 7:
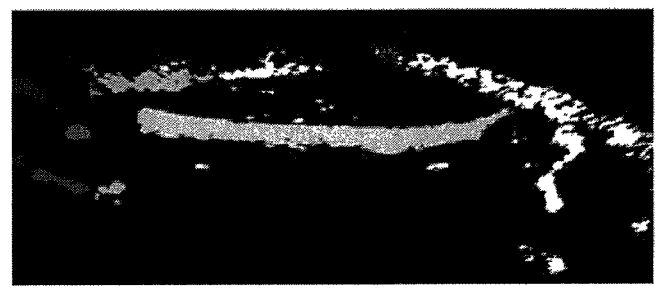
FIG. 7 illustrates a labeled binary image.

FIG. 7 illustrates a labeled binary image.

Referring to FIG. 7, each of the plurality of segments in the binary image is labeled using a different gray level. However, FIG. 7 is only an illustration of labeling, and the binary image may be labeled using various methods. For example, each of the plurality of segments may be labeled using a number.

Next, the data processor 120 may determine one of the plurality of segments as the target image based on image characteristics of the target bone. A segment having the most image characteristics of the target bone from among the plurality of segments is determined as the target image that is an image of the target bone.

Since the target bone has higher reflectivity than surrounding tissue, the image of the target bone has a higher luminance value than the other regions. Thus, the data processor 120 may determine a segment having the highest luminance value from among the plurality of segments as the target image. In detail, the data processor 120 may obtain a sum of luminance values of points belonging to each of the plurality of segments and determine a segment of which a sum of luminance values is the greatest as the target image.

A sum $S_L$ of luminance values of each segment may be represented by Equation 5 below.

$$S_L = \Sigma_{p \in L} CEh(p) \qquad (5)$$

In Equation 5, L denotes an index of a segment, and p denotes a point.

When the target image is determined, the data processor 120 may display black for the residual part excluding the segment determined as the target image.

Figure 8:
FIG. 8 illustrates a binary image in which only a target image is displayed.

FIG. 8 illustrates a binary image in which only the target image is displayed.

The data processor 120 may measure the length of the target bone based on the determined target image.

Figure 9:
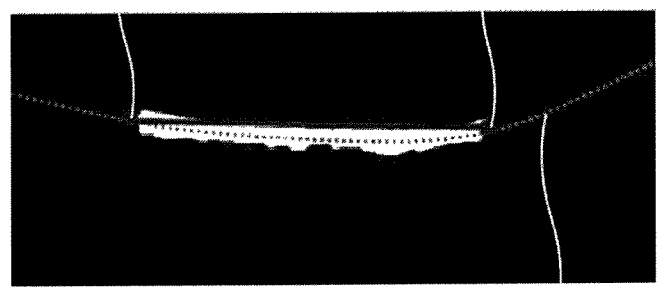
FIG. 9 illustrates a method of measuring a length of a target bone based on the target image.

FIG. 9 illustrates a method of measuring the length of the target bone based on the target image.

Referring to FIG. 9, the data processor 120 may acquire a measurement line 11 by skeletonizing the target image. The data processor 120 may measure the length of the target bone based on a distance between a first point 12a and a second point 12b that are intersection points between the target image and the measurement line 11.

However, FIG. 9 is only illustrative, and the data processor 120 may detect both end points 12a and 12b in a long axis direction of the target image by using various methods to measure the length of the target bone based on a distance between both end points 12a and 12b.

A case where the image data is two-dimensional data has been described. Hereinafter, a case where the image data is volume data will be described.

Figure 10:
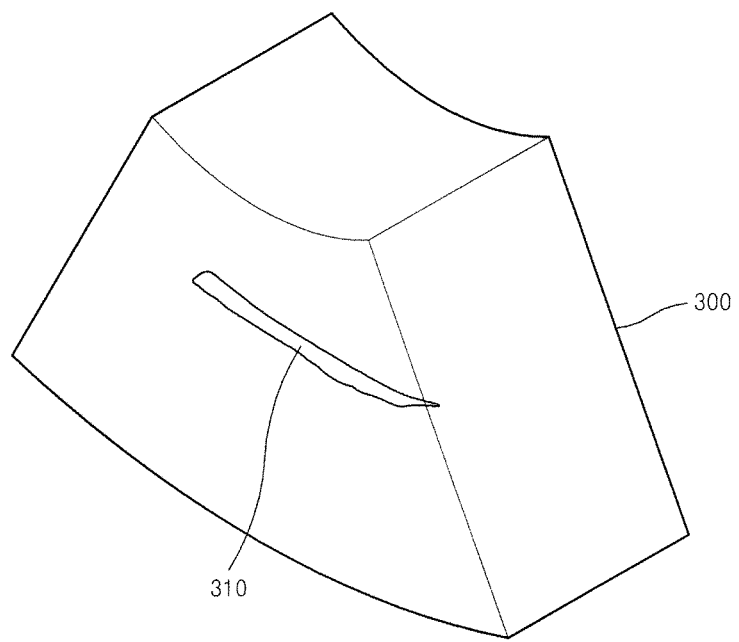
FIG. 10 illustrates volume data.

FIG. 10 illustrates volume data 300.

Referring to FIG. 10, the volume data 300 includes a target image 310 that is a three-dimensional image of a target bone. Although the target image 310 is clearly shown in FIG. 10 for convenience of description, a boundary of a target image in actual volume data may not be clear due to noise or the like.

While pixel values are processed for two-dimensional image data, voxel values are processed for volume data. Except for this, a method of processing two-dimensional image data may be applicable to volume data. Thus, a method of processing volume data, which is equivalent to the method of processing two-dimensional image data, will be described in brief, and a processing method exclusive to volume data will be mainly described in detail.

The data processor 120 may acquire binary volume data from the volume data by performing thresholding. Before acquiring the binary volume data, the top-hat transformation, the contrast enhancement, and so forth described above may be performed, and thereafter, an adaptive threshold may be applied.

The binary volume data includes the target image and may further include an image of other tissue having another shape. Thus, image processing for extracting the target image from the binary volume data may be performed as described below.

The data processor 120 may perform labeling of the binary volume data. The binary volume data is segmented into a plurality of segments by labeling, wherein each of the plurality of segments is a three-dimensional region including points whose luminance values are 1. The plurality of segments are candidates of the target image.

The data processor 120 may determine one of the plurality of segments as the target image. A segment having the most image characteristics of the target bone from among the plurality of segments is determined as the target image.

The image characteristics of the target bone may include shape information and a luminance value.

The data processor 120 may analyze shapes of the plurality of segments and acquire one or more remaining segments from among the plurality of segments based on the analyzed shapes. Thereafter, the data processor 120 may determine one of the one or more remaining segments as the target image based on luminance values.

Figure 11:
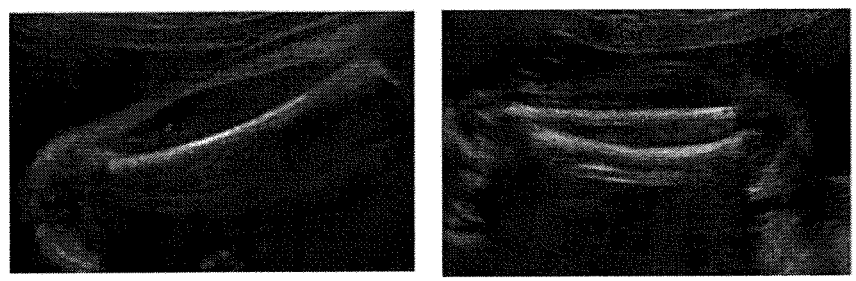
FIG. 11 illustrates various shapes of target images.

FIG. 11 illustrates various shapes of target images.

Referring to FIG. 11, each target image has a linear tubular shape or a curved tubular shape.

To analyze a shape of each of the plurality of segments, the data processor 120 may perform principle component analysis (PCA) for each of the plurality of segments. The PCA is one of methods of analyzing a data set and is useful to detect a distribution pattern of data. The PCA is an analysis method for representing information regarding data to be more easily viewed by determining a direction in which a variance of the data is maximized and contracting the data based on the determined direction. The PCA involves linear transforming of data to a new coordinate system in which an axis by which a variance of the data is the greatest when the data is projected towards one axis is a first coordinate axis, and an axis by which a variance of the data is the second greatest when the data is projected towards one axis is a second coordinate axis.

The data processor 120 may obtain a direction and magnitude of a first principle component, a direction and magnitude of a second principle component, and a direction and magnitude of a third principle component for each of the plurality of segments through the PCA. In tubular shaped data, the magnitude of the first principle component is relatively large, and magnitudes of the second and third principle components are relatively small. Thus, the data processor 120 may analyze a shape of each of the plurality of segments based on the magnitudes of the first to third principle components.

A tube-score $T_S$ may be defined by Equation 6 using the first to third principle components.

$$T_S = 1 - \frac{\lambda_2 - \lambda_3}{\lambda_1^2} \quad (6)$$

In Equation 6, $T_S$ denotes a tube-score, $\lambda_1$ denotes a magnitude of a first principle component, $\lambda_2$ denotes a magnitude of a second principle component, and $\lambda_3$ denotes a magnitude of a third principle component.

The data processor 120 may obtain a tube-score for each of the plurality of segments and determine segments whose tube-score is greater than a critical value from among the plurality of segments as one or more remaining segments. That is, segments whose tube-score is equal to or less than the critical value are excluded from target image candidates. The critical value may be empirically set. For example, the critical value may be set to 0.997.

The data processor 120 acquires one or more remaining segments from the plurality of segments based on the analyzed shapes and one of the one or more remaining segments as the target image based on the luminance values.

The data processor 120 may determine a segment whose luminance value is the greatest from among the one or more remaining segments as the target image. In detail, the data processor 120 may obtain a sum of luminance values of points belonging to each of the one or more remaining segments and determine a segment of which the sum of luminance values is the greatest as the target image.

The data processor 120 excludes some of the plurality of segments from candidates by analyzing shapes of the plurality of segments before determining the target image. By doing this, a segment having a relatively large magnitude may be prevented from being wrongly selected as the target image.

The data processor 120 may measure the length of the target bone based on the determined target image.

However, images of a plurality of long bones may exist in the binary volume data. In the method described above, the data processor 120 may measure a length of the longest bone that is a reference, i.e., the target bone. Next, the data processor 120 may select images of other long bones based on the length of the target bone and measure lengths of the other long bones.

Next, a method of measuring the length of the target bone based on the determined target image will be described.

The data processor 120 may determine a longitudinal section of the target image and measure the length of the target bone based on the longitudinal section because the length of the target bone should be measured on the longitudinal section of the target image to accurately measure the length of the target bone.

To determine a specific plane in a three-dimensional space, at least three points, which are not on one direct line, are needed. Thus, to determine the longitudinal section of the target image, three or more points on the longitudinal section are determined. Next, a method of determining three points on a longitudinal section will be described with reference to FIG. 12.

Figure 12:
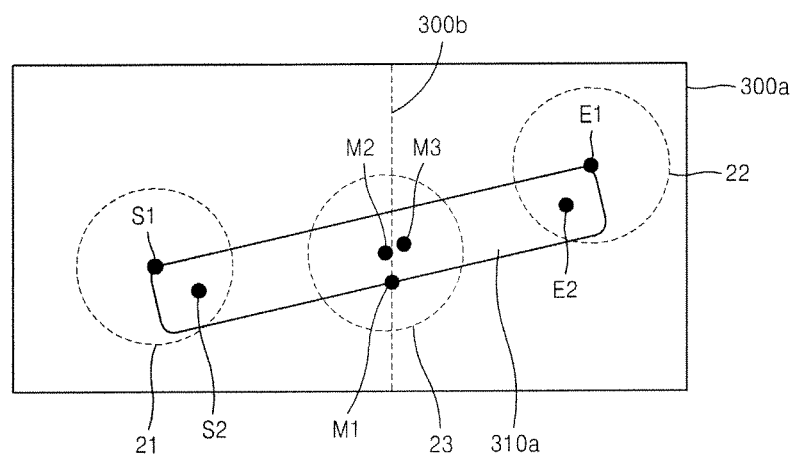
FIG. 12 illustrates a horizontal cross-section of the volume data.

FIG. 12 illustrates a horizontal cross-section of volume data 300*a*.

Referring to FIG. 12, the volume data 300*a* includes a segment determined as a target image 310*a*. The data processor (120 of FIG. 1) acquires a mean point M1 corresponding to a mean coordinate of all points belonging to the target image 310*a*. The data processor 120 may acquire both end points S1 and E1 farthest from each other from among the points belonging to the target image 310*a* based on a vertical section 300*b* passing through the mean point M1. The vertical section 300*b* is a vertical cross-section of the volume data 300*a*, which passes through the mean point M1.

The data processor 120 sets spheres 21 and 22, whose centers are both end points S1 and E1, for both end points S1 and E1. The data processor 120 acquires a first point S2 and a second point E2, which correspond to mean coordinates of points belonging to the target image 310*a* and the spheres 21 and 22, for the spheres 21 and 22, respectively. A radius of each of the spheres 21 and 22 may be set so that points belonging to the target image 310*a* and each of the spheres 21 and 22 are appropriately defined. For example, one-third of a distance between both end points S1 and E1 may be set as a radius of each of the spheres 21 and 22.

The data processor 120 acquires a point M2, whose distance from the first point S2 is equal to a distance from the second point E2, from among the points belonging to the target image 310*a*. That is, the distance between the first point S2 and the point M2 is equal to the distance between the second point E2 and the point M2. A plurality of points whose distance from the first point S2 is equal to a distance from the second point E2 may exist from among the points belonging to the target image 310a. The data processor 120 may acquire any one of the plurality of points as the point M2.

The data processor 120 sets a sphere 23 whose center is the point M2. The data processor 120 acquires a third point M3, which corresponds to a mean coordinate of points belonging to the target image 310a and the sphere 23.

The data processor 120 may determine a cross-section passing through the first point S2, the second point E2, and the third point M3 as a longitudinal section of the target image 310a. In addition, the data processor 120 may measure a length of a target bone based on a distance between the first point S2 and the second point E2.

FIG. 12 illustrates an example of a method of determining a longitudinal section of a target image, and the longitudinal section of the target image may be determined using various methods.

Figure 13:
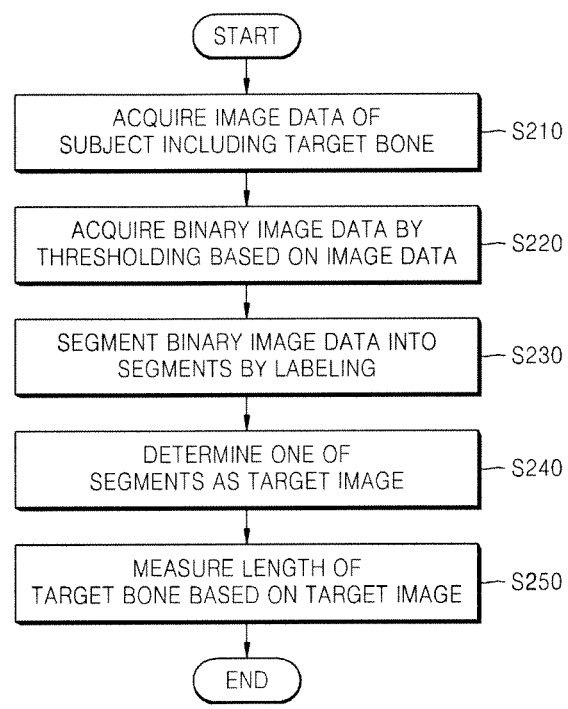
FIG. 13 is a flowchart illustrating an image processing method according to another embodiment of the present invention.

FIG. 13 is a flowchart illustrating an image processing method according to another embodiment of the present invention.

Referring to FIG. 13, in operation S210, image data of a subject including a target bone is acquired. In operation S220, binary image data is acquired by performing thresholding based on the image data. In operation S230, the binary image data is segmented into a plurality of segments by labeling. In operation S240, one of the plurality of segments is determined as a target image based on image characteristics of the target bone. In operation S250, a length of the target bone is measured based on the target image.

The image processing method of FIG. 13 may be performed by the image processing apparatus of FIG. 1. The description given with reference to FIGS. 1 to 12 may be applied to operations S210 to S250 in the image processing method. Thus, a description thereof will not be repeated here.

As described above, according to an embodiment of the present invention, an image processing apparatus and method for efficiently measuring a length of a target bone may be provided.

An image processing apparatus according to an embodiment of the present invention may automatically measure a length of a target bone by automatically extracting a target image that is an image of the target bone based on image data. This is more efficient than a case where a user manually measures a length of a target bone while viewing an image. In the manual measurement, a measurement deviation may occur according to a skill of the user and a subjective determination of the user. In addition, in the manual measurement, a time taken for measurement may be long. According to an embodiment of the present invention, since a length of a target bone is automatically measured, accuracy of the measurement may increase. In addition, a time taken for measurement may be reduced.

Furthermore, the image processing apparatus according to an embodiment of the present invention may automatically extract a target image from volume data and automatically determine a longitudinal section from the target image. If a user manually finds a longitudinal section of a target bone, it is difficult to guarantee accuracy due to a deviation between users. In addition, when the user needs to repeat scanning to find the longitudinal section, a chance that the user suffers a repetitive stress injury (RSI) may increase. Thus, according to an embodiment of the present invention, accuracy of measurement may increase. In addition, the chance that the user suffers an RSI may decrease.

According to embodiments of the present invention, an image processing apparatus for efficiently measuring a length of a target bone and an operating method thereof may be provided.

The method described above may be written as computer programs and may be implemented in general-use digital computers that execute the programs using a computer-readable recording medium. In addition, a data structure used in the method described above may be written in a computer-readable recording medium in various manners. Examples of the computer-readable recording medium include storage media such as magnetic storage media (e.g., ROM, RAM, USB, floppy disks, hard disks, etc.), optical recording media (e.g., CD-ROMs, or DVDs, etc.) and PC interfaces (e.g., PCI, PCI-express, Wi-Fi, etc.).

It will be understood by one of ordinary skill in the art that various changes in form and details may be made herein without departing from the spirit and scope of the present invention as defined by the following claims. The exemplary embodiments should be considered in a descriptive sense only and not for purposes of limitation. Therefore, the scope of the present invention is defined not by the detailed description of the present invention but by the appended claims, and all differences within the scope will be construed as being included in the present invention.

What is claimed is:

1. An image processing apparatus comprising:
a data acquisition device for acquiring image data of a subject including a target bone; and
a data processor for segmenting the image data into a plurality of segments, determining one of the plurality of segments as a target image based on image characteristics of the target bone, determining a longitudinal section of the target image, the longitudinal section passing through a center of the target image, and measuring a length of the target bone based on the longitudinal section.

2. The image processing apparatus of claim 1, wherein the image data is volume data, and
the data processor analyzes shapes of the plurality of segments, acquires one or more remaining segments from the plurality of segments based on the analyzed shapes, and determines one of the one or more remaining segments as the target image based on luminance values.

3. The image processing apparatus of claim 2, wherein the data processor acquires a magnitude of a first principal component, a magnitude of a second principal component, and a magnitude of a third principal component for each of the plurality of segments by performing principal component analysis (PCA) on each of the plurality of segments to analyze the shapes of the plurality of segments and acquires the one or more remaining segments based on the magnitudes of the first to third principal components.

4. The image processing apparatus of claim 3, wherein the data processor obtains a tube-score defined based on the magnitudes of the first to third principal components for each of the plurality of segments and determines segments of which tube-score is greater than a critical value from among the plurality of segments as the one or more remaining segments.

5. The image processing apparatus of claim 4, wherein the tube-score is defined by $$T_S = 1 - \frac{\lambda_2 - \lambda_3}{\lambda_1^2},$$

where $\lambda_1$ denotes the magnitude of the first principal component, $\lambda_2$ denotes the magnitude of the second principal component, and $\lambda_3$ denotes the magnitude of the third principal component.

6. The image processing apparatus of claim 5, wherein the data processor determines a segment of which a luminance value is the greatest from among the one or more remaining segments as the target image.

7. The image processing apparatus of claim 6, wherein the segment determined as the target image is a segment of which a sum of luminance values of points belonging thereto is the greatest.

8. The image processing apparatus of claim 1, wherein the data processor acquires binary image data by performing thresholding based on the image data, segmenting the binary image data into a plurality of segments by labeling.

9. The image processing apparatus of claim 8, wherein the data processor acquires a mean point corresponding to a mean coordinate of points belonging to the target image, acquires both end points farthest from each other on a vertical section of the volume data, which passes through the mean point, from among the points belonging to the target image, sets spheres of which the centers are the both end points, acquires a first point and a second point corresponding to mean coordinates of points belonging to the spheres and the target image for the spheres, acquires a point whose distance from the first point is equal to a distance from the second point from among the points belonging to the target image, sets a sphere whose center is the point, acquires a third point corresponding to a mean coordinate of points belonging to the sphere and the target image, and determines a section passing through the first, second, and third points as the longitudinal section of the target image.

10. The image processing apparatus of claim 9, wherein the data processor measures the length of the target bone based on a distance between the first and second points.

11. The image processing apparatus of claim 1, wherein the data processor acquires an adaptive threshold value based on a mean and a standard deviation of luminance values based on the image data and acquires the binary image data by performing the thresholding based on the adaptive threshold value.

12. The image processing apparatus of claim 11, wherein the data processor performs top-hat transformation and contrast enhancement based on the image data before performing the thresholding.

13. The image processing apparatus of claim 12, wherein the data processor performs denoising on the image data before performing the top-hat transformation.

14. The image processing apparatus of claim 13, wherein the image data is two-dimensional image data, and
the data processor determines a segment of which a luminance value is the greatest from among the plurality of segments as the target image.

15. The image processing apparatus of claim 14, wherein the segment determined as the target image is a segment of which a sum of luminance values of points belonging thereto is the greatest.

16. The image processing apparatus of claim 15, wherein the data processor detects both end points in a long axis of the target image and measures the length of the target bone based on a distance between the both end points.

17. An image processing method comprising:
acquiring image data of a subject including a target bone;
segmenting the image data into a plurality of segments;
determining one of the plurality of segments as a target image based on image characteristics of the target bone;
determining a longitudinal section of the target image, the longitudinal section passing through a center of the target image; and
measuring a length of the target bone based on the longitudinal section.

18. The image processing method of claim 17, wherein the image data is volume data, and
the determining comprises:
analyzing shapes of the plurality of segments and acquiring one or more remaining segments from the plurality of segments based on the analyzed shapes; and
determining one of the one or more remaining segments as the target image based on luminance values.

19. The image processing method of claim 18, wherein the segmenting comprises:
acquiring binary image data by performing thresholding based on the image data; and
segmenting the binary image data into a plurality of segments by labeling.

20. A non-transitory computer readable recording medium having recorded thereon a program for executing the image processing method of claim 17.

* * * * *